United States Patent [19]

Osmalov et al.

[11] Patent Number: 5,228,462
[45] Date of Patent: Jul. 20, 1993

[54] CIGARETTE INSPECTION DEVICE

[75] Inventors: Jerome S. Osmalov; Bhanu M. Evani, both of Richmond; Herbert C. Longest, Jr., Midlothian, all of Va.

[73] Assignee: Philip Morris Incorporated, New York, N.Y.

[21] Appl. No.: 889,457

[22] Filed: May 27, 1992

[51] Int. Cl.⁵ .............................................. A24C 5/32
[52] U.S. Cl. .................................... 131/280; 131/905; 131/908; 209/535
[58] Field of Search .............. 131/280, 905, 907, 908; 209/522, 523, 529, 535, 577, 587; 250/216

[56] References Cited

U.S. PATENT DOCUMENTS

| | | |
|---|---|---|
| 3,483,873 | 12/1969 | Hinzmann . |
| 3,527,234 | 8/1970 | Hinzmann . |
| 4,011,950 | 3/1977 | McLoughlin et al. . |
| 4,208,578 | 6/1980 | McLoughlin et al. . |
| 4,277,678 | 7/1981 | Wahle et al. . |
| 4,398,546 | 8/1983 | Fisher et al. . |
| 4,403,620 | 9/1983 | Joseph et al. . |
| 4,484,591 | 11/1984 | Wahle et al. . |
| 4,574,958 | 3/1986 | Manservisi . |
| 4,639,592 | 1/1987 | Heitmann . |
| 4,767,924 | 8/1988 | Giebel et al. . |
| 4,901,860 | 2/1990 | Wahle et al. . |

FOREIGN PATENT DOCUMENTS

| | | | |
|---|---|---|---|
| 1110268 | 4/1968 | United Kingdom | ............... 209/535 |
| 2221029A | 1/1990 | United Kingdom . | |

OTHER PUBLICATIONS

Pattern Processing Technologies, Inc., 400 Vision Process Controller ™, Beta Release Documentation, 1991.

Primary Examiner—V. Millin
Assistant Examiner—Jennifer Doyle
Attorney, Agent, or Firm—Ronald A. Krasnow

[57] ABSTRACT

Inspection of completed cigarettes is accomplished by the cigarettes traveling on a rolling drum past a single stationary rolling block with preferably two cameras connected to a vision system. The first camera views the cigarette before the rolling block, the cigarette is then rolled approximately 180° and then the second camera views the previously hidden portion of the cigarette. Cigarettes are accepted or rejected based on a comparison of the viewed cigarettes to a predetermined set of characteristics.

16 Claims, 2 Drawing Sheets

CIGARETTE INSPECTION DEVICE

BACKGROUND OF THE INVENTION

This invention relates to an apparatus and method for the inspection of cigarettes. More particularly, this invention relates to inspection of cigarettes using a rolling drum and a rolling block to expose nearly 360° of a cigarette for a machine vision system to view cigarettes at two positions.

It is well known to test cigarettes or other rod shaped smoking articles prior to introduction into boxes or packets for sale to consumers. The testing is for quality control and is intended to uncover unsatisfactory conditions in the cigarettes, such as stem holes, skewed or torn tipping, tobacco under the rod seam, torn ends on the cigarette, and spots from glue, flavors or oil. It is the goal of cigarette manufacturers to eliminate these unsatisfactory conditions.

Quality control in cigarette production must continually advance as the speed of cigarette production increases. Inspection systems must also advance to accommodate the faster speeds of production. Therefore, while prior systems are known, these systems do not always perform completely satisfactorily at the higher speeds of current cigarette production. Further, the known testing methods may not test for some unsatisfactory conditions. Current inspection devices rely on pressure drops to find unsatisfactory conditions such as loose ends, missing filters and stem holes. However, they do not test for all the unsatisfactory conditions listed above.

Tobacco smoking articles, such as cigarettes and cigars, are made into rods on machines which take cut filler that is formed into a continuous rod of tobacco, and encircles the tobacco with a continuous ribbon of paper which is glued and heat-sealed. The continuous tobacco rod is formed and sealed in the making machine and then proceeds to another processing machine, such as a tipper. The tipper attaches a filter plug cut to the appropriate length between two tobacco rods. The tipper applies glue and wraps tipping paper around the filter segment and a portion of the tobacco rods. This creates a double cigarette length. The two cigarettes are then cut and oriented into a single row. A tipper as described is shown, for example, in U.S. Pat. No. 3,527,234 to Hinzmann. It is the completed cigarette that is inspected for unsatisfactory conditions.

Optical scanning of cigarettes during production is taught by U.S. Pat. No. 4,277,678 to Wahle et al. There, a cigarette is inspected in the tipping machine by two optoelectrical units mounted on a single rolling drum. The cigarette is stopped in its path and rotated using a separate rotary element while the optoelectrical units scan the cigarette's wrapper for unsatisfactory conditions. Each optoelectrical unit scans the entire cigarette for particular unsatisfactory conditions.

Other cigarette inspection systems test the cigarettes at several testing stations. Each station tests the cigarette for one or two different types of unsatisfactory conditions. U.S. Pat. Nos. 4,403,620 to Joseph et al., 4,484,591 to Wahle et al. and 4,901,860 to Wahle et al. all teach separate testing stations for different unsatisfactory conditions in cigarettes.

Still other cigarette inspection systems use more than one drum to create more than one inspection zone. U.S. Pat. No. 4,639,592 to Heitman passes cigarettes before optical inspection devices located at certain points along a predetermined path. The path requires at least two vacuum drums each to expose one side of the cigarette. Note that Heitman specifically prefers to not mechanically rotate the cigarette. Great British Patent No. 2,221,029 teaches a similar method.

Further, other devices inspect cigarettes before they are completed. For example, U.S. Pat. No. 4,350,170 to Baier teaches inspection of the cigarette rod as it comes off the rod making machine by passing the rod through an annular housing. A similar device is taught by U.S. Pat. No. 4,208,578 to McLoughlin et al.

None of the devices known currently in the field, inspect cigarettes in the simple, effective, compact system as disclosed herein. This invention provides a method and apparatus to inspect cigarettes at the speeds of modern production while inspecting nearly the entire cigarette.

SUMMARY OF THE INVENTION

In view of the above, it is an object of this invention to provide an apparatus and method to visually inspect completed cigarettes.

It is another object of this invention to provide an apparatus and method to that will automatically reject assembled cigarettes that do not meet inspection standards.

It is a further object of this invention to provide an apparatus and method to visually inspect nearly 360° of the circumference of the assembled cigarette.

It is yet another object of this invention to provide an apparatus and method to visually inspect nearly the entire surface of an assembled cigarette in a compact, efficient space employing a minimum of equipment.

These and other objects that will be apparent to one of ordinary skill in the art are met by a machine vision system comprising at least two-dimensional video cameras to inspect cigarettes at two positions on a single rolling drum, preferably as part of the tipper. There is at least one rolling block that works in conjunction with the rolling drum to roll the cigarette.

In the preferred operation, the first rolling block attaches a filter plug to the tobacco rods, as part of the standard tipping operation of the tipper. Located after the first rolling block is a first two-dimensional video camera to inspect nearly the entire first half of the completed single- or double-length cigarette. A second rolling block is then provided to roll the cigarette approximately 180°. Located after the second rolling block is a second two-dimensional video camera to inspect nearly the entire second half of the cigarette.

In an alternative embodiment, a rolling drum can be provided after the tipper to provide the space needed for a first inspection, rolling the completed cigarette and then a second inspection. This drum could also be located just at the end of the tipper.

The vision system determines, from the information provided by the video cameras, whether the cigarette meets the preset characteristics for a completed cigarette. If the cigarette does not meet those characteristics, the cigarette is removed from the cigarette manufacturing system by a delivery/reject drum. The delivery/reject drum is located directly after the rolling drum and may be conventional.

The invention provides a compact, efficient system for inspecting completed cigarettes at the high speeds of production encountered in today's modern manufacturing systems.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION

Figure 1:
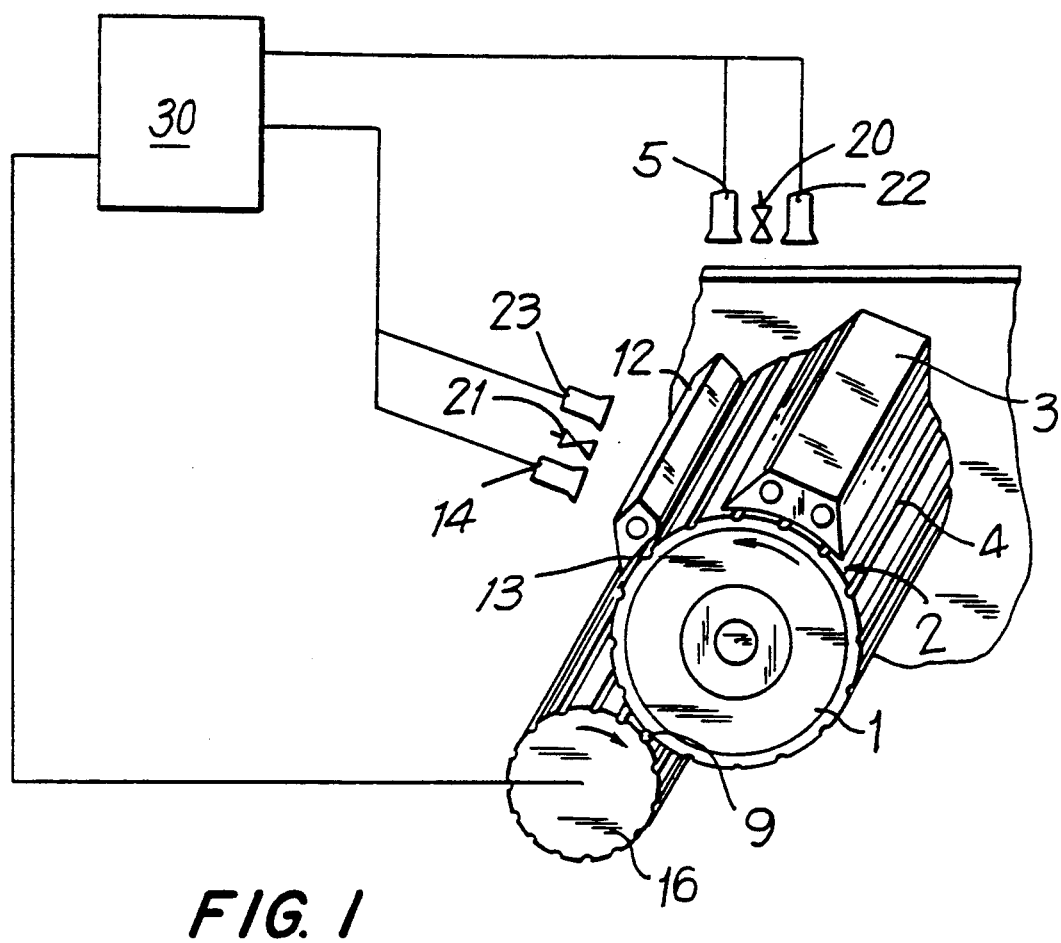
FIG. 1 is a view of the invention isolated from the other parts of the tipper.

FIG. 1 shows the components of this invention. There is a rolling drum 1 that is preferably a suction drum. The drum has a peripheral rolling surface 2, which is caused, by a drive means (not shown), to advance at a constant angular speed in a preferably counterclockwise direction. On the rolling surface 2, there are a plurality of successive axially parallel flutes 4 spaced from each other by identical distances. The flutes 4 extend at right angles to the direction of travel of the rolling surface 2. Also, each of the flutes 4 is arranged to hold tobacco rods, double-length cigarettes or single-length cigarettes in place. The drum 1 is rotatable on a shaft (not shown) that extends to a conventional part of the tipper. The drive means for the rolling drum is also a conventional part of the tipper. In alternative embodiments, it should be understood that while certain details are considered conventional to the tipper, those details would be provided for if the embodiment of the invention being considered did not reside on the tipper.

It should also be understood that although double-length cigarettes are referred to throughout this description to describe a preferred embodiment of this invention, one of ordinary skill in the art will appreciate that single-length cigarettes could also be inspected using this invention. As such, the term "completed cigarette" will be used to mean any cigarette whether single or double-length, and whether attached to a filter or not.

Figure 2:
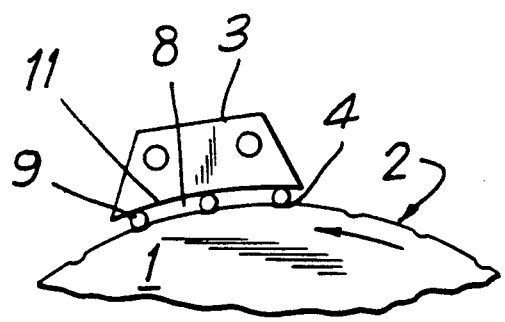
FIG. 2 is detailed view of a rolling block working in conjunction with the rolling drum.

Working in conjunction with the rolling drum 1 is a first rolling block 3. The first rolling block 3 is preferably a stationary block having a concave counter-surface 11 cooperating with the rolling surface 2 to define therewith an elongated curved channel or gap 8 best shown in FIG. 2. The gap 8 between the first rolling block 3 and the rolling drum 1 has a length sufficient to roll the tipping paper and attach the filter plug to the tobacco rods. The width of the gap 8 is less than the diameter of the completed cigarette so that the two surfaces cause the cigarette to roll during travel through the gap 8. There are several auxiliary pieces of equipment that serve to feed the tobacco rods and filter plugs to the rolling drum and the invention. There is also auxiliary equipment to remove the completed cigarettes from the rolling drum. Such auxiliary equipment is conventional, and described, for example, in U.S. Pat. No. 3,527,234 to Hinzmann.

The depth of flutes 4 on the rolling drum 1 is only a fraction of the width of the gap 8. Each flute 4 is in communication with the intake ends of several radial suction ducts (not shown) and the inner or discharge ends of suction ducts. These ducts provide suction to attract the tipping paper, the tobacco rods and the filter plugs. The suction from the ducts holds the cigarettes against the force of gravity and centrifugal force while they travel along the rolling drum 1 before and after tipping and inspection.

After the filter plug has been attached to the tobacco rods, the completed cigarette 9 moves clear of the first rolling block 3 as it rests in its respective flute 4, held there by the suction ducts. The complete cigarette 9 is then first inspected by this invention. It will be appreciated by one of skill in the art that should the rolling drum be located at the end of or after the tipper, then the first inspection by this invention will be after the completed cigarette is transferred to the rolling drum. A first camera 5 is provided, as shown in FIG. 1, to view the cigarette on the rolling surface 2 and is preferably two-dimensional. The first camera 5 has a lens arranged to receive light reflected off of the cigarette 9 as cigarette 9 travels past the first camera 5.

In a preferred embodiment, there is a light source 20 attached to first camera 5. The light source 20 is arranged such that the light radiation is directed towards the portion of the rolling surface 2 focused on by the first camera 5. The light source 20 provides sufficient light to allow each cigarette length to reflect enough light for the camera to properly operate, thereby allowing inspection.

Figure 3:
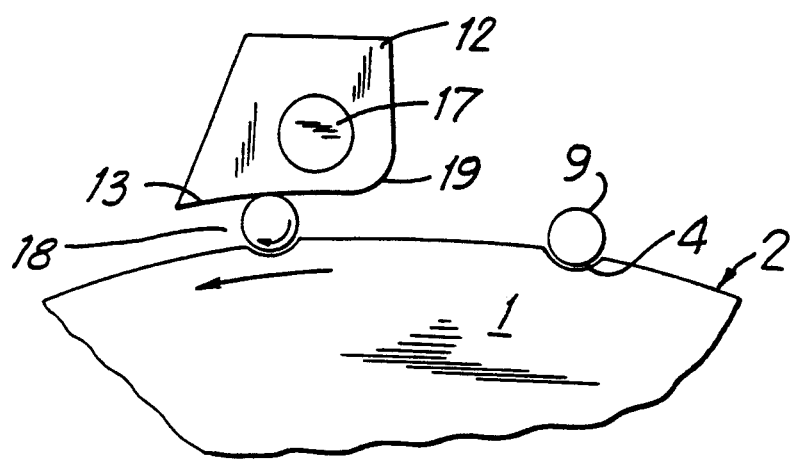
FIG. 3 is a detailed view of the second rolling block working in conjunction with the rolling drum.

The cigarette 9 remains in its respective flute 4 as the rolling drum 1 continues in a preferably counterclockwise direction. After inspection by the first camera 5, the cigarette 9 is rolled approximately 180° by a second rolling block 12 working in conjunction with the rolling drum 1. As shown in FIG. 3, the second rolling block 12 is preferably a stationary block and has a concave counter-surface 13 cooperating with the rolling surface 2 to define therewith an elongated curved channel or gap 18. The gap 18 between the counter-surface 13 and the rolling surface 2 has an arc length sufficient to roll the cigarette 9 by approximately 180° from its position before entering the gap 18. The gap 18 has a width that is less than the diameter of the cigarette 9 so that the surfaces defining the gap cause the cigarette 9 to roll during travel through the gap. The concave counter-surface 13 has a surface that provides sufficient friction to rotate, but not damage, the cigarette 9. The counter-surface 13 has a front edge 19 to receive the cigarette 9. As the rolling surface 2 preferably travels in a counterclockwise direction, the cigarette 9 rolls in a preferably clockwise direction in its respective flute 4. While the rolling block 12 is described as stationary, it need only be stationary with respect to the rolling drum 1. In a preferred embodiment, the rolling block 12 is attached in an adjustable manner by an attachment means 17. The attachment means 17 allows the rolling block 12 to be adjusted for different cigarette diameters.

After the cigarette 9 has been rotated, the invention, as shown in FIG. 1, provides for a second camera 14, preferably two-dimensional, to inspect nearly 180° of the cigarette. In a preferred embodiment, there is a light source 21 attached to the second camera 14. The light source 21 is arranged such that the light given off is directed towards the portion of the rolling surface 2 focused on by the second camera 14. The light source 21 provides sufficient light to allow each cigarette to reflect enough light for the second camera 14 to properly operate, thereby allowing inspection.

The cameras 5, 14 are video cameras that may be conventional as known to those skilled in the art. The first camera 5 is placed such that the lens of the camera views the cigarette after the cigarette has moved past the first rolling block. The second camera 14 is placed such that the lens of the camera views the cigarette after it has been rotated approximately 180° by the second rolling block 12. Each camera views nearly 180° of the circumference of the cigarette 9. Therefore, since the portion of the cigarette 9 hidden to the first camera 5, is inspected by the second camera 14, nearly the entire cigarette is inspected on a single rolling drum.

In a preferred embodiment, in addition to the individual cameras 5 and 14, there are third and fourth cameras 22, 23. The third camera 22 is arranged to view the cigarette at the same location on the rolling surface 2 as the first camera 5 and is also connected to the vision system 30. The fourth camera 23 arranged to view the cigarette at the same location on the rolling surface 2 as the second camera 14. More than one camera viewing the cigarette at each inspection point allows more than 180° of inspection of the cigarette's circumference. Thus, it is possible to inspect the entire cigarette circumference. Alternatively, any method to get two views of the completed cigarette at each of the two inspection points will allow for inspection of the entire cigarette circumference.

A vision system 30 is employed in this invention and may be conventional. The vision system 30 is connected to each of the first and second cameras 5, 14 to receive the signals outputted by the camera as a result of their having viewed the cigarette 9. Generally, the information received from the cameras is compared to a predetermined set of characteristics. The vision system 30 determines such characteristics and unsatisfactory conditions as stem holes, skewed or torn tipping, spots from glue, flavors or oil, tobacco under the rod seam, torn ends on the cigarette end, and the dimensions of the cigarette (including its length and diameter). For example, a vision monitoring system such as that produced by Pattern Processing Technologies, Inc., model 400 VPC TM will serve the purposes of this invention. See also U.S. Pat. No. 3,049,588 to Barnett for a camera system used to inspect and compare an object to a standard.

After the second camera inspection, the cigarette 9 passes to a delivery/reject unit. As shown in FIG. 1, this comprises at least a delivery/reject drum 16. The delivery/reject drum 16 is a second vacuum drum with a traveling surface that rolls in a direction opposite from that of the rolling drum 1. The delivery/reject drum 16 receives the cigarette 9 from the rolling drum 1. In response to signals received from the vision system 30, the cigarette 9 is either rejected or, preferably, delivered by the delivery/reject drum to another part of the tipper that divides double-length cigarettes into two single-length cigarettes. Delivery of completed cigarettes by the delivery/reject drum can be to any machinery that directly follows the delivery/reject drum. For example, in an alternative embodiment, the invention may be located just upstream of a cigarette packer, and then the delivery/reject drum would deliver approved completed cigarettes directly to the packer.

A cigarette 9 is rejected if it does not meet the predetermined set of characteristics programmed into the vision system. Rejected completed cigarettes are sent to a recycle unit for recycling of at least the tobacco. Transfer of the cigarette 9 between the rolling drum 1 and the delivery/reject drum 16 may be conventional. See for example, U.S. Pat. No. 3,527,234 to Hinzmann.

The signals received from the vision system may also be conventional. See for example U.S. Pat. No. 3,049,588 to Barnett.

It is clear that while two rolling blocks are discussed, the invention only requires one rolling block for inspection of a cigarette. One of ordinary skill in the art will appreciate that this invention can be employed using any rolling surface and relative stationary block with two cameras and a vision system. While particular embodiments of the invention have been presented, it should be understood that various changes and modifications to the apparatus and method can be made without departing from the scope and spirit of the invention.

What is claimed is:

1. An apparatus for inspection of cigarettes comprising:
   a rolling drum having a traveling rolling surface with a plurality of successive flutes spaced from each other by identical distances and extending at right angles to the direction of travel of said rolling surface, each of said flutes being arranged to receive a cigarette;
   drive means for said rolling drum;
   a rolling block having a counter-surface defining with said rolling surface a gap through which said cigarette advances, the width of said gap being less than the diameter of said cigarette so that said surfaces cause said cigarette to roll during travel through said gap;
   a first camera arranged to view said cigarette before entering said gap;
   a second camera arranged to view said cigarette after exiting said gap, wherein each of said first and second cameras outputs a first signal;
   a vision system coupled to said first and second cameras, wherein said vision system receives said first signals from said cameras, to compare said first signals to a predetermined set of characteristics, and output a second signal based on said comparison; and
   a delivery/reject unit having a delivery/reject drum to receive said cigarette from said rolling surface, said unit also coupled to receive said second signal from said vision system for rejecting cigarettes that do not comply with said predetermined set of characteristics.

2. The apparatus of claim 1 wherein the arc length of said gap is sufficient to roll the cigarette approximately 180° from its position before entering said gap.

3. The apparatus of claim 1, additionally comprising a first light source proximate to said first camera.

4. The apparatus of claim 1, additionally comprising a second light source proximate to said second camera.

5. The apparatus of claim 1, additionally comprising third and fourth cameras, said third camera arranged to view said cigarette at the same location on said rolling surface as said first camera and connected to said vision system, and said fourth camera arranged to view said cigarette at the same location on said rolling surface as said second camera and connected to said vision system.

6. The apparatus of claim 2, additionally comprising a first light source proximate to said first camera.

7. The apparatus of claim 2, additionally comprising a second light source proximate to said second camera.

8. A method of inspecting cigarettes comprising the steps of providing a cigarette on a rolling surface, viewing said cigarette a first time with a first camera, rolling said cigarette approximately 180° with a rolling block, viewing said cigarette a second time, sending a first signal as a result of said first and second viewings to a vision system, comparing said first signal to a predetermined set of characteristics, transferring said cigarette to a delivery/reject unit, sending a second signal based on said comparison from said vision system to said delivery/reject unit and rejecting said cigarettes that do not comply with said predetermined set of characteristics.

9. The method of claim 8, wherein said step of viewing said cigarette a second time comprises use of a second camera.

10. The method of claim 8, wherein said step of viewing said cigarette a first time comprises viewing nearly 180° of the circumference of said cigarette.

11. The method of claim 8, wherein said step of viewing said cigarette a second time comprises viewing nearly 180° of the circumference of said cigarette.

12. The method of claim 8, wherein said step of viewing said cigarette a first time comprises viewing at least 180° of the circumference of said cigarette.

13. The method of claim 8, wherein said step of viewing said cigarette a second time comprises viewing at least 180° of the circumference of said cigarette.

14. The method of claim 8, wherein said step of rolling said cigarette comprises providing a rolling block with a counter-surface cooperating with said rolling surface to define therewith a gap, said rolling surface moving said cigarette through said gap, and said gap having a length sufficient to roll said cigarette by approximately 180° from its position before entering said gap.

15. The method of claim 14, wherein said rolling block in said step of rolling said cigarette is stationary.

16. The method of claim 15, wherein said rolling surface travels in a counterclockwise direction and said cigarette rolls in a clockwise direction.

* * * * *